(12) United States Patent
Cherkassky

(10) Patent No.: US 6,641,572 B2
(45) Date of Patent: Nov. 4, 2003

(54) INTERSTITIAL SPACE SATURATION

(75) Inventor: Michael Cherkassky, 1550 W. Rosedale Suite 418, Ft. Worth, TX (US) 76104

(73) Assignee: Michael Cherkassky, Fort Worth, TX (US)

( * ) Notice: Subject to any disclaimer, the term of this patent is extended or adjusted under 35 U.S.C. 154(b) by 98 days.

(21) Appl. No.: 10/054,573

(22) Filed: Jan. 24, 2002

(65) Prior Publication Data

US 2003/0139728 A1 Jul. 24, 2003

(51) Int. Cl.[7] .............................................. A61M 31/00
(52) U.S. Cl. .................. 604/509; 604/508; 604/28; 604/96.01
(58) Field of Search ...................... 604/28, 500, 506, 604/508, 509, 96.01, 912, 915

(56) References Cited

U.S. PATENT DOCUMENTS

| | | | |
|---|---|---|---|
| 4,192,302 A | | 3/1980 | Boddie |
| 4,714,460 A | | 12/1987 | Calderon |
| 4,867,742 A | | 9/1989 | Calderon |
| 4,883,459 A | * | 11/1989 | Calderon ...................... 604/28 |
| 5,391,143 A | * | 2/1995 | Kensey ...................... 604/5.03 |
| 5,395,314 A | * | 3/1995 | Klatz et al. ................... 604/24 |
| 2002/0107504 A1 | * | 8/2002 | Gordon ...................... 604/507 |
| 2003/0120202 A1 | * | 6/2003 | Gordon ...................... 604/28 |

OTHER PUBLICATIONS

Ausman et al., "Isolated Perfusion of the Liver with Hn2", Surgical Forum 1959, vol. x, pp. 77–79.
Chung et al., "A Technique of Islated Perfusion of the Liver," Surgery 1962, vol. 51, No. 4, pp. 508–511.
Stehlin JS Jr, Clark RL. Experiences with regional chemotherapy: Perfusion and intra–arterial infusion. Arch Surg 1962; 85:84–94.
Intra–arterial BCNU chemotherapy for treatment of malignant gliomas of the central nervous system Greenberg HS, Ensminger WD, Chandler WF, et al. J Neurosurg 61:423–429, 1984.
C. Karakousis et al., "Tourniquet Infusion Chemotherapy for Osseous Malignant Lesions", Cancer Drug Delivery 1985, vol. 2, pp35–47.

* cited by examiner

Primary Examiner—Brian L. Casler
Assistant Examiner—Jeremy Thissell

(57) ABSTRACT

Providing a means for perfusing a high concentration of medication to treat a lesion, specifically cancer, infection, or autoimmune process, while averting the leakage of a substantial quantity of medication into the general blood stream. The process prevents toxic levels of the agent from entering the body's general circulation while delivering lethal doses of the agent to the lesion.

4 Claims, 4 Drawing Sheets

INTERSTITIAL SPACE SATURATION

CROSS-REFERENCE TO RELATED APPLICATIONS

Not applicable.

1. Background—Field of Invention

This invention relates to treatment of a lesion, specifically cancer, through the introduction of a high concentration of medication to a specific area. It will also have wide applicability in the treatment of infectious processes such as leprosy, tuberculosis, AIDS and other viral, fungal and bacterial diseases.

2. Background—Description of Prior Art

Traditional intravenous methods of treatment are not designed to allow a high concentration of medication (chemotherapeutic agent) to be directed to a specific area without allowing the majority of the agent to escape into the bloodstream. Present chemotherapy methods entail introducing the medication into the venous flow, whereby the medical agent passes through the affected cancerous area and continues through the bloodstream to be distributed to the entire body. Consequently, the same concentration of medication that affects the cancerous area also affects the remainder of the body. As a result, healthy cells of the organism are affected to the same degree as the cancerous cells. The process does not allow complete eradication of the tumor and forces the treatments to be halted without achieving the full desired potency of the medical agent on the cancerous cells. Vital parts of the organism could be destroyed along with the cancer if the treatments are continued.

Several attempts have been made to circumvent the problems associated with existing methods of cancer treatment. Goals associated with these endeavors include increasing the concentration of medication in the target area and minimizing the concentration on the periphery. Attempts have been made to introduce the chemotheraputic agent through an injection using an indwelling catheter inserted percutaneously and directed to the tumor. An external tourniquet is applied for five minutes on the treated extremity. This action temporarily stops, or decreases, the arterial blood flow and confines the chemotherapeutic agent to the regional tissue, while simultaneously blocking the venous return. (C. Karakousis, Cancer Drug Delivery, 1985).

The logic of our critique follows that after the tourniquet is removed, the regular blood flow begins to disseminate the medication throughout the body. Five minutes of exposure is insufficient for the medication to exert a marked effect on the tumor.

Other attempts introduced the medication intra-arterially to the corresponding area of the lesion. (Greenberg, H. S., et al, Journal of Neurosurgery, 1984). Following this process, however, the medication would escape into the main blood stream after the first pass, producing the exact same effects as those plaguing the present methods.

Further improvement of the above method, introducing the medication intra-arterially, involves isolated perfusion with the simultaneous collection of venous blood from the same area. This process re-circulates, or detoxifies, the venous blood. Constant and lengthy perfusion of a specific, given area, is now permitted, preventing dissemination of the medication to the rest of the body by shunting blood through the lesion via the arterio-venous axis as discussed in U.S. Pat. No. 4,192,302 (1980). (Stehlin, J. S., Arch Surg, 1962). Unfortunately these methods bypass interstitial space where the lesion resides.

Another method, created by Reynaldo Calderon in U.S. Pat. No. 4,867,742 (1989) and U.S. Pat. No. 4,714,460 (1987), places focus on the introduction of the medication intravenously in the retrograde fashion. However, problems arise from the necessity to reverse the blood flow in the vein in order to bring the medication upstream. Immense pressure is required to assure delivery of the medical agent to the capillary level.

The capillary, which functions at a pressure of approximately 7 mm of mercury, is now forced to endure a pressure between 120 and 150 mm of mercury, the usual systolic blood pressure. As a result the tissue will be destroyed before the medication is delivered. For these reasons this method is unsuccessful.

SUMMARY

All of the above-described methods disregard the anatomical and physiological relationships inside the body, utilizing a one-dimensional mode of circulation: arterial-to-venous. In truth, though, blood is delivered to the periphery by the arterial system. The outflow is assured by two separate systems, venous and lymphatic (FIG. 1). In order to reach the lesion, it is necessary to traverse interstitial space, the area where the cells of the organs are located and in which the lesion (cancer) resides. A cure is only possible when direct contact between the medication and the cancer is maintained for a prolonged period of time, while sparing the rest of the body.

OBJECTS AND ADVANTAGES

Medication introduced by the previously-described methods bypasses the interstitial space, keeping medication inside the arterio-venous axis, preventing it from penetrating into the interstitial space. Allowing the maximum quantity of medication into the interstitial space is the only method to keep a therapeutic concentration of the drug in contact with the lesion. The neoplastic growth (cancer) resides within the interstitial area as do bacteria, fungi, and viruses. All our efforts should be focused on this region (FIG. 2).

DESCRIPTION OF INVENTION

Figure 1:
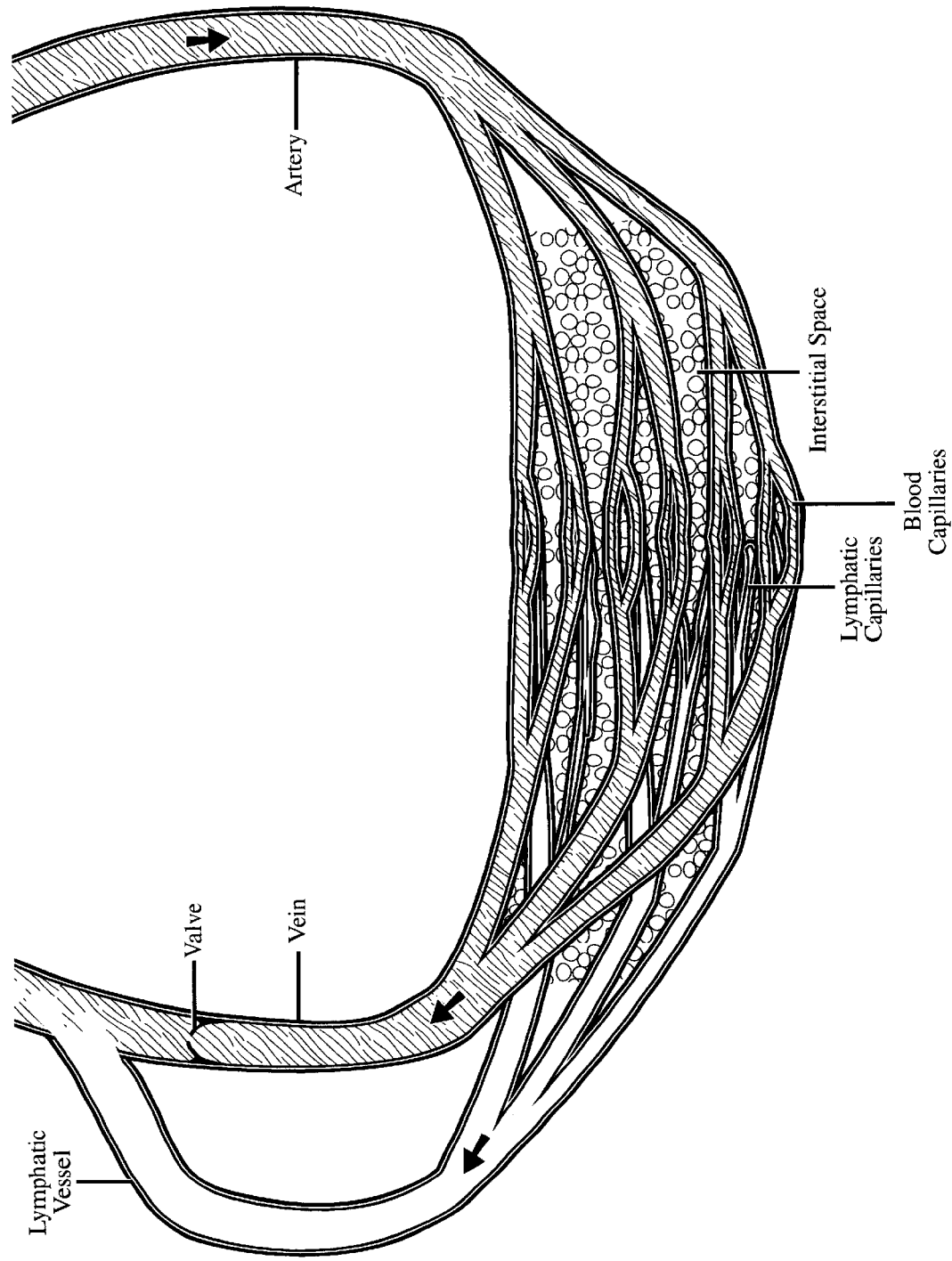
FIG. 1 displays the schematic representation of blood circulation, in which blood flows arterially to the periphery and returns to the heart by both the venous and lymphatic pathways. It also displays relations between arterial supplies, venous and lymphatic drainage and interstitial space.
Figure 2:
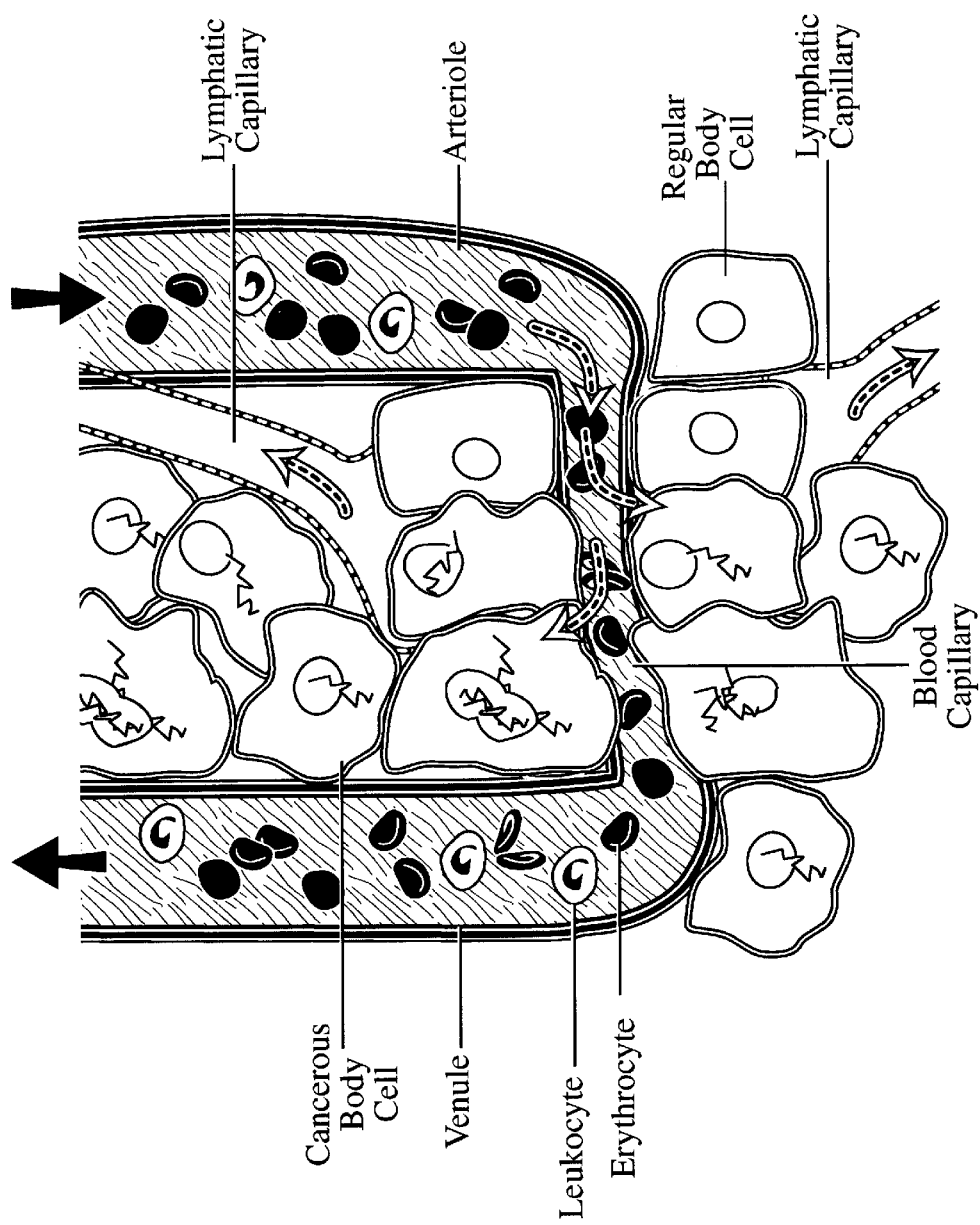
FIG. 2 depicts a detailed representation of the direction of blood flow and lymphatic drainage. It shows interstitial space and its relation to blood and lymphatic circulation as well as the location of cancer cells in the interstitial space.
Figure 3:
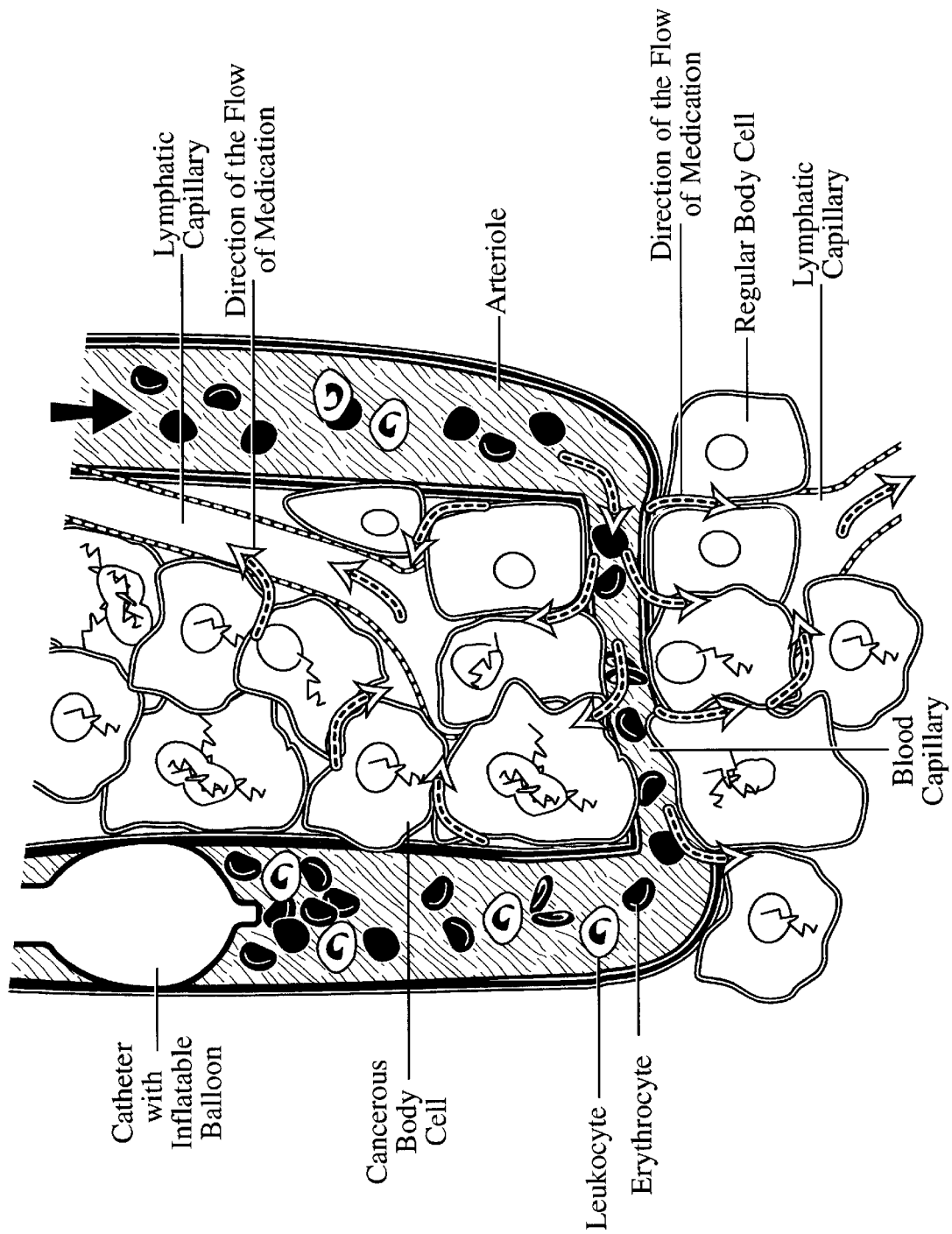
FIG. 3 illustrates the interstitial space, including the residing cancer cells, and the introduction of the medication intra-arterially. By blocking the venous outflow with a balloon, the medication is shunted into the interstitial space with a subsequent diversion to the lymphatic vessels.

This is a novel approach of introducing medication into the interstitial area and a lesion. The medical agent is introduced intra-arterially while blocking the venous outflow. The initial step is to take an arteriogram, which yields a graphic representation of the internal loops within the blood flow and aids in determining the preferential drainage. A permanent intra-arterial catheter is then inserted into the designated artery. The process continues with insertion of a catheter with an inflatable balloon, via an external vein, into the preferential venous drainage of a solid tumor. Subsequent infusion of medication intra-arterially will follow. Medication will inescapably be forced to go through the capillary wall into the interstitial space due to the total blockage of the venous outflow by the inflated balloon. Medication will eventually drain into the lymphatic system and be collected in one of the large lymph vessels. Introduction of medication into the lymphatic system allows the treatment process to follow the metastatic spread, thus greatly reducing the possibility of distant metastases (FIG. 3). Further improvement of the above method may be achieved with the removal of the corresponding lymph fluids through the balloon catheter, assuring closed circulation.

The introduction into the interstitial space can be facilitated by the forceful drainage of the lymphatic fluid through the catheter in the lymph vessel. This creates a negative suction pressure for fluids on the lymphatic side of the arterio-capillary-lymphatic axis.

Figure 4:
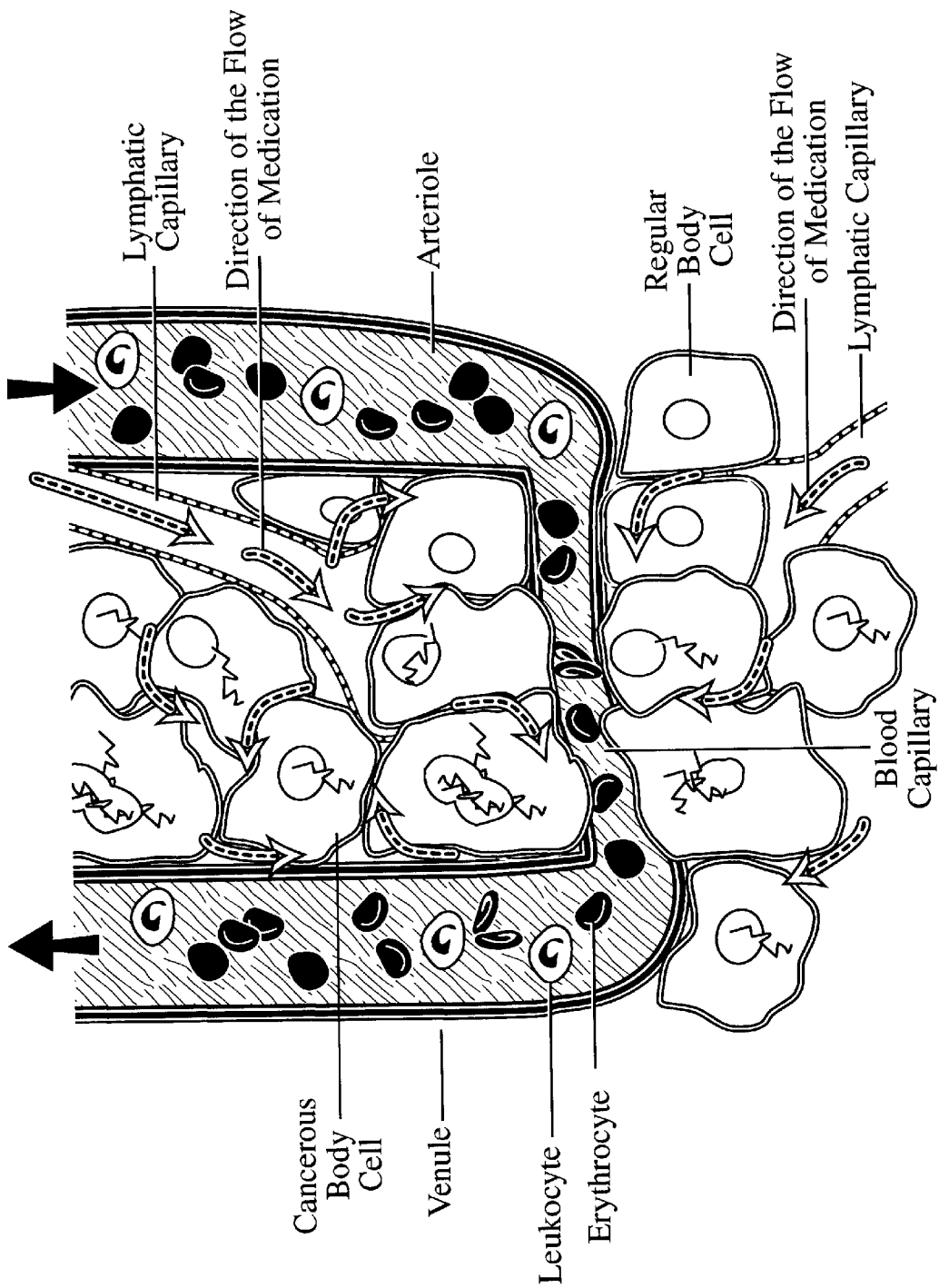
FIG. 4 portrays retrograde infusion of medication into the lymphatic vessels and subsequent introduction of medication into the interstitial space, corresponding to the area of the lesion.

It is also possible to introduce medication in a retrograde fashion into corresponding lymphatic vessels at the location of the lesion in order to achieve a high concentration of medication in the interstitial space. Pressure within lymphatic vessels is close to zero, negating the problems faced with the venous retrograde method (FIG. 4). Removing the lymphatic fluid prior to the introduction of the medication will further facilitate this method.

Advantages

Focusing within interstitial space and controlling both outflow routes, venous and lymphatic, allows almost complete isolation of the target area and total control of the timing and concentration of the medication. Saturating the interstitial area with medication for prolonged periods of time will affect only the targeted lesions and assure the safety of the patient. Specifically, the process protects sensitive anatomical parts (bone marrow, nervous system) from being injured by the medication (chemotherapy).

Conclusion, Ramifications and Scope

Accordingly, the reader will see that the new method offers a revolutionary way of treating various diseases, which the art of medicine, at present, is not able to conquer.

Concentration of medication in the area where abnormal growth or infection are located delivers the maximal effect to the lesion, while avoiding harm to the rest of the organism.

Though this invention has been described with emphasis on the treatment of cancer, it is quite apparent that it has broader applications. The invention is useful for the treatment of any organ in which the treating agent would cause toxic effects if it entered the general circulation. For example, the invention could be applied to the treatment of diseases such as leprosy, AIDS, pulmonary anthrax and other bacterial, viral and fungal infections. There is also a role for treatment of certain types of hematologic cancers, such as leukemia and lymphomas.

The foregoing disclosure and description of the invention are illustrative and explanatory thereof, and various changes in the size, shape and materials, as well as in the details of the illustrated construction may be made without departing from the spirit of the invention.

I claim:

1. A method for perfusing a high concentration of medication through a target area in the patient's body comprising the steps of:

a) inserting percutaneously a single catheter into an artery supplying a target area;

b) placing a catheter, having spaced balloon into a vein of the body near the target area;

c) inflating said balloon in order to totally block the flow of venous blood in said vein;

d) injection a medication from said arterial catheter into said artery; whereby a channeling of the complete amount of medication into interstitial space via arterial-capillary-lymphatic access is achieved and concentration within the body's general circulation is minimized.

2. The method of claim 1, further including the steps of:

a) placing a catheter having suction lumen and spaced balloon into a lymphatic vessel of the body near the target area;

b) inflating said balloon to isolate effluent lymph fluid from the target area from the body's general circulation;

c) removing from the body through said lymphatic catheter said effluent lymph liquid, containing said medication, from said target area;

d) treating said removed effluent lymph fluid to reduce the quantity of said medication returning the thus said treated lymph fluid to the body via intravenous routes.

3. The method of claim 2 further including the step of suctioning said lymph fluid of said target area prior to the introduction of the said medication in order to create a negative pressure to facilitate the penetration of said medication through capillary wall.

4. A method for perfusing a high concentration of medication through a target area in the patient's body without contaminating the body's general circulation, comprising the steps of:

a) placing a catheter having a suction-infusion lumen and spaced balloon with said spaced balloon positioned proximally from said lumen into a lymphatic vessel of the body near the target area;

b) inflating said balloon to isolate effluent lymph fluid from the target area from the body's general circulation;

c) suctioning said lymph fluid from said lymphatic vessel creating a negative pressure in said lymphatic vessel of said target area;

d) injecting said medication into said lymphatic vessel;

e) removing from the body through said catheter said medication after sufficient exposure;

whereby irrigation of the interstitial space of said target area is achieved without affecting the rest of the body and 100% concentration of medication remains within the lesion.

* * * * *